US00PP28867P3

(12) United States Plant Patent
Koning

(10) Patent No.: US PP28,867 P3
(45) Date of Patent: Jan. 9, 2018

(54) ***LAVANDULA* PLANT NAMED 'ANNET'**

(50) Latin Name: *Lavandula angustifolia*
Varietal Denomination: Annet

(71) Applicant: Lammert Koning, Nuis (NL)

(72) Inventor: Lammert Koning, Nuis (NL)

(73) Assignee: L. KONING BEHEER B.V., Nuis (NL)

( * ) Notice: Subject to any disclaimer, the term of this patent is extended or adjusted under 35 U.S.C. 154(b) by 0 days.

(21) Appl. No.: 14/999,141

(22) Filed: Mar. 31, 2016

(65) Prior Publication Data

US 2017/0290251 P1 Oct. 5, 2017

(51) Int. Cl.
*A01H 5/02* (2006.01)

(52) U.S. Cl.
USPC ..... Plt./445

(58) Field of Classification Search
USPC ..... Plt./445
See application file for complete search history.

(56) References Cited

PUBLICATIONS

PLUTO Plant Variety Database . Mar. 2, 2017. p. 1.*

* cited by examiner

*Primary Examiner* — Annette Para
(74) *Attorney, Agent, or Firm* — C. A. Whealy

(57) ABSTRACT

A new and distinct cultivar of *Lavandula* plant named 'Annet', characterized by its compact and broadly upright plant habit; relatively rapid growth rate; freely branching growth habit; strong durable plants; freely flowering habit; violet-colored flowers arranged on terminal spikes; relatively long flowering period; and good garden performance.

2 Drawing Sheets

Botanical designation: *Lavandula angustifolia.*
Cultivar denomination: 'ANNET'.

BACKGROUND OF THE INVENTION

The present invention relates to a new and distinct *Lavandula* plant, botanically known as *Lavandula angustifolia*, commonly referred to as Lavender and hereinafter referred to by the name 'Annet'.

The new *Lavandula* plant is a product of a planned breeding program conducted by the Inventor in Nuis, The Netherlands. The objective of the breeding program was to develop new unique *Lavandula* plants with good performance and attractive plant form and flower coloration.

The new *Lavandula* plant originated from a cross-pollination made by the Inventor in June, 2009 of *Lavandula angustifolia* 'Blue Royalty', disclosed in U.S. Plant Pat. No. 20,657, as the female, or seed, parent with *Lavandula angustifolia* 'Maxima', not patented, as the male, or pollen, parent. The new *Lavandula* plant was discovered and selected by the Inventor as a single flowering plant within the progeny of the stated cross-pollination in a controlled environment in Nuis, The Netherlands in August, 2010.

Asexual reproduction of the new *Lavandula* plant by terminal cuttings in a controlled greenhouse environment in De Lier, The Netherlands since September, 2011 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Annet' as a new and distinct *Lavandula* plant:

1. Compact and broadly upright plant habit.
2. Relatively rapid growth rate.
3. Freely branching growth habit.
4. Strong durable plants.
5. Freely flowering habit.
6. Violet-colored flowers arranged on terminal spikes.
7. Relatively long flowering period.
8. Good garden performance.

Plants of the new *Lavandula* differ primarily from plants of the female parent, 'Blue Royalty', in inflorescence size and peduncle thickness as plants of 'Blue Royalty' have smaller inflorescences and thinner peduncles.

Plants of the new *Lavandula* differ primarily from plants of the male parent, 'Maxima', in peduncle thickness as plants of 'Maxima' have thicker peduncles.

Plants of the new *Lavandula* can be compared to plants of the *Lavandula angustifolia* 'Hidcote Blue', not patented. In side-by-side comparisons, plants of the new *Lavandula* differ primarily from plants of 'Hidcote Blue' in the following characteristics:

1. Plants of the new *Lavandula* are more compact and denser than plants of 'Hidcote Blue'.
2. Plants of the new *Lavandula* flower for a longer period of time than plants of 'Hidcote Blue'.
3. Plants of the new *Lavandula* have shorter and thicker peduncles than plants of 'Hidcote Blue'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet is a side perspective view of a typical flowering plant of 'Annet' grown in a container.

The photograph on the second sheet is a close-up view of a typical inflorescence of 'Annet'.

DETAILED BOTANICAL DESCRIPTION

Plants used in the aforementioned photographs and following detailed description were grown in 12-cm containers during the spring and early summer in an outdoor nursery in Boskoop, The Netherlands and under cultural practices typical of commercial *Lavandula* production. Plants were nine months old when the photographs and description were taken. During the production of the plants, day temperatures ranged from 10° C. to 30° C. and night temperatures ranged from 5° C. to 20° C. In the following description, color references are made to The Royal Horticultural Society Colour Chart, 2007 Edition, except where general terms of ordinary dictionary significance are used.

Botanical classification: *Lavandula angustifolia* 'Annet'.

Parentage:

*Female, or seed, parent.*—*Lavandula angustifolia* 'Blue Royalty', disclosed in U.S. Plant Pat. No. 20,657.

*Male, or pollen, parent.*—*Lavandula angustifolia* 'Maxima', not patented.

Propagation:

*Type*.—Terminal vegetative cuttings.

*Time to initiate roots, summer and winter*.—About ten days at temperatures about 18° C.

*Time to produce a rooted young plant, summer*.—About 60 days at temperatures about 20° C.

*Time to produce a rooted young plant, winter*.—About 70 days at temperatures about 20° C.

*Root description*.—Fine, fibrous; initially white in color and becoming more brown with development; actual color of the roots is dependent on substrate composition, water quality, fertilizer type and formulation.

*Rooting habit*.—Freely branching; dense.

Plant description:

*Plant and growth habit*.—Herbaceous perennial; compact and broadly upright plant habit; freely branching habit; moderately vigorous growth habit; relatively rapid growth rate; flowers arranged in verticillasters on terminal spikes.

*Plant height, soil level to top of floral plane*.—About 39.4 cm.

*Plant width*.—About 41.5 cm.

*Lateral branch description*.—Quantity per plant: About 64 primary lateral branches developing per plant. Length: About 11.9 cm. Diameter: About 3 mm. Internode length: About 2.8 cm. Strength: Strong. Aspect: Upright to outwardly. Texture and luster: Smooth, glabrous; slightly glossy. Color, developing: Close to 137C. Color, developed: Close to between N199A and N199B.

*Leaf description*.—Arrangement: Opposite, simple; sessile. Length: About 5.3 cm. Width: About 9 mm. Shape: Lanceolate to narrowly oblanceolate. Apex: Broadly acute to obtuse. Base: Cuneate. Margin: Entire; slightly revolute. Texture and luster, upper and lower surfaces: Smooth, glabrous; very slightly glossy. Fragrance: Strongly aromatic, pungent. Venation pattern: Pinnate. Color: Developing leaves, upper surface: Close to 143A. Developing leaves, lower surface: Close to between 143C and 144A. Fully expanded leaves, upper surface: Close to N137B; venation, close to 138A to 138B. Fully expanded leaves, lower surface: Close to N137D; venation, close to 137C.

Flower description:

*Flower type, arrangement and habit*.—Small single salverform flowers arranged in verticillasters on terminal spikes; freely flowering habit with about 325 flowers developing per inflorescence and more than 6,000 flowers developing per plant; flowers with two-lobed upper lip and three-lobed lower lip; flowers face mostly outward to slightly upright on the spike.

*Natural flowering season*.—Relatively long flowering period; continuous from late spring into the summer in The Netherlands.

*Flower longevity on the plant*.—Individual flowers last about ten days on the plant; flowers not persistent.

*Fragrance*.—None detected.

*Flower buds*.—Length: About 6 mm. Diameter: About 3 mm. Shape: Oblong. Texture and luster: Moderately tomentose; matte. Color: Close to 83A.

*Inflorescence height*.—About 8.8 cm.

*Inflorescence diameter*.—About 2.6 cm.

*Flower diameter*.—About 8 mm.

*Flower depth (height)*.—About 1.2 cm.

*Petals*.—Quantity and arrangement: Upper lip, two-lobed and lower lip, three-lobed. Length, upper lip: About 1.2 cm. Length, lower lip: About 1.1 cm. Width, upper lip: About 3 mm. Width, lower lip: About 2 mm. Shape: Roughly spatulate; lower 66.7% fused into a tube. Apex: Obtuse, rounded. Margin: Entire. Texture and luster, upper (inner) surface: Smooth, glabrous, velvety; matte. Texture and luster, lower (outer) surface: Sparsely pubescent, velvety; matte. Color: When opening and fully opened, upper (inner) surface: Close to 86D; throat, close to 84C to 84D, towards the base, close to NN155D; color does not fade with development. When opening and fully opened, lower (outer) surface: Close to 86D; tube, close to N78C to N78D, towards the base, close to NN155D; color does not fade with development.

*Basal flower bracts*.—Quantity and arrangement: Each group of flowers is subtended by a single basal flower bract. Length: About 5 mm. Width: About 4.5 mm. Shape: Broadly rhomboidal. Apex: Aristate. Base: Cuneate. Margin: Entire. Texture and luster, upper and lower surfaces: Smooth, glabrous; matte. Color, upper and lower surfaces: Close to 157D; towards the margins, tinged with close to 86A to 86B; venation, close to 143B.

*Sepals*.—Quantity and arrangement: Five, fused into a campanulate tube. Calyx length: About 4 mm. Calyx diameter: About 2 mm. Shape: Lanceolate. Apex: Broadly acute. Margin: Entire. Texture and luster, upper (inner) and lower (outer) surfaces: Densely pubescent; matte. Color: When opening and fully opened, upper (inner) surface: Close to 83A; pubescence, close to 83A. When opening and fully opened, lower (outer) surface: Close to 145D; venation, close to 144B; pubescence, close to 83A.

*Peduncles*.—Length: About 22.8 cm. Diameter: About 2.5 mm. Aspect: Mostly upright. Strength: Strong to slightly outward. Texture and luster: Smooth, glabrous; slightly glossy. Color: Close to 137C.

*Reproductive organs*.—Stamens: Quantity per flower: Four. Filament length: About 2 mm. Filament color: Close to NN155D. Anther shape: Reniform. Anther length: About 0.75 mm. Anther color: Close to 203D. Pollen amount: Moderate to abundant. Pollen color: Close to 17A. Pistils: Quantity per flower: One. Pistil length: About 3.5 mm. Stigma shape: Club-shaped. Stigma color: Close to 152A. Style length: About 3 mm. Style color: Close to 157B to 157D. Ovary color: Close to 143A.

*Seeds and fruits*.—Seed and fruit production has not been observed on plants of the new *Lavandula*.

Disease & pest resistance: Plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be hardy to USDA Hardiness Zone 6.

It is claimed:

1. A new and distinct *Lavandula* plant named 'Annet' as illustrated and described.

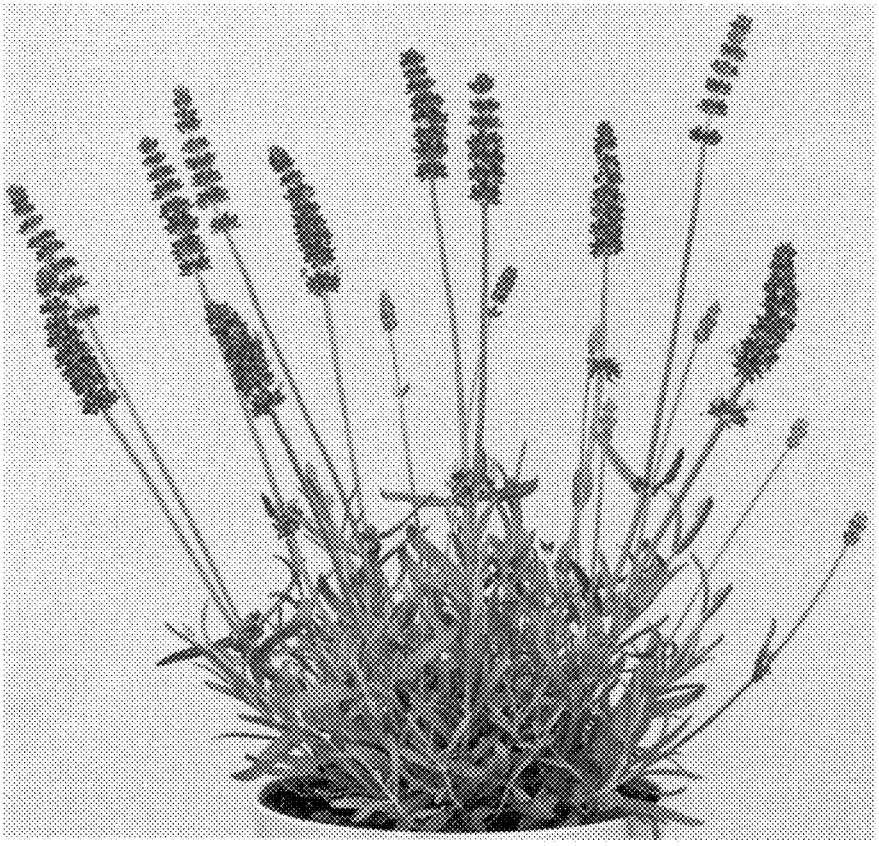

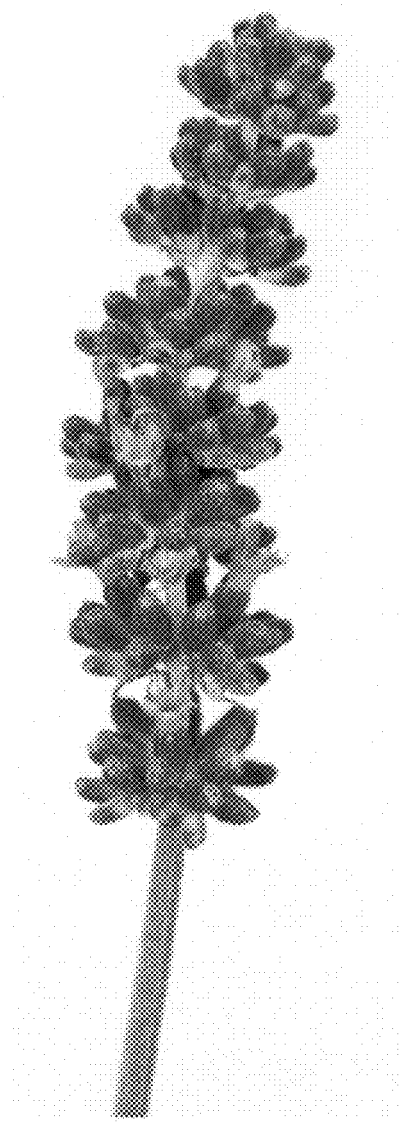

* * * * *